United States Patent [19]

Pruett et al.

US005103058A

[11] Patent Number: 5,103,058
[45] Date of Patent: Apr. 7, 1992

[54] PROCESS FOR PRODUCING IMINES AND/OR AMINES FROM ALCOHOLS

[75] Inventors: Roy L. Pruett, Harrisburg, N.C.; Michael J. Keenan, Baton Rouge, La.; Edmund J. Mozeleski, Califon, N.J.

[73] Assignee: Exxon Chemical Patents Inc, Linden, N.J.

[21] Appl. No.: 609,209

[22] Filed: Nov. 5, 1990

[51] Int. Cl.$^5$ .................................. C07C 251/08
[52] U.S. Cl. .................. 564/248; 564/278; 564/479; 564/480; 564/478
[58] Field of Search ............ 564/248, 480, 478, 278, 564/279, 479; 568/485, 486, 487, 488, 489

[56] References Cited

U.S. PATENT DOCUMENTS

| | | | |
|---|---|---|---|
| 2,422,013 | 6/1947 | Haury et al. | 564/279 |
| 2,513,996 | 7/1950 | Haury et al. | 564/279 |
| 4,152,353 | 5/1979 | Haberman | 260/585 B |
| 4,210,605 | 7/1980 | Hoshino et al. | 564/473 |
| 4,788,347 | 11/1988 | Sagou et al. | 568/487 |

FOREIGN PATENT DOCUMENTS

WO85/02173 5/1985 PCT Int'l Appl. .

Primary Examiner—Richard L. Raymond
Assistant Examiner—Shailendra Kumar

[57] ABSTRACT

Process for producing aliphatic imines and/or amines from aliphatic monohydric alcohols, such as higher molecular weight oxo alcohols, including ether alcohols, comprising the steps of dehydrogenating the alcohol to an aldehyde in situ in the presence of a zinc oxide and/or zinc salt/metal hydroxide dehydrogenation catalyst and a soluble amount of a primary aliphatic amine which condenses immediately with the aldehyde under reflux conditions, with continuous water removal, to form the corresponding aliphatic imine (Schiff base). The corresponding aliphatic amine can be formed by reducing or reductively aminating the imine in known manner to form corresponding primary, secondary or tertiary amines as desired. The step of forming the imine is most critical, and the present zinc/metal hydroxide dehydrogenation catalyst system has been found to provide a gentle, inexpensive and efficient conversion of the alcohol to the aldehyde for reaction with the gradually-added primary amine, coupled with the continuous removal of the water of condensation in order to prevent undesired secondary reactions which reduce the yield.

29 Claims, No Drawings

PROCESS FOR PRODUCING IMINES AND/OR AMINES FROM ALCOHOLS

BACKGROUND OF THE INVENTION

1. Field of the Invention

The present invention relates to a novel process for producing aliphatic imines and/or amines, particularly those having a high molecular weight, from monohydric aliphatic alcohols and ether alcohols, particularly oxo alcohols having a high molecular weight, including dimer alcohols, as produced by the reaction of olefin feedstock in the oxo process. The oxo process involves the reaction of olefins with carbon monoxide and hydrogen to form predominantly aldehydes, which are converted to alcohols and other chemicals.

High molecular weight amines have a variety of utilities including the production of surfactants, wetting agents, intermediates, etc. However the production of such amines in high yield generally is difficult, requiring expensive catalyst systems and/or high temperatures and pressures.

2. Discussion of Prior Art

Processes for producing amines from aldehydes, ketones or alcohols, comprising reacting them with an aminating agent in the presence of a dehydrogenation catalyst, are well known. However many of the known processes are expensive, inefficient, inoperative for the production of high molecular weight and/or branched amines, and/or require harsh reaction conditions.

In most known processes for converting alcohols, particularly high molecular weight alcohols and branched alcohols, to amines by reaction with aminating agents such ammonia, it is difficult to obtain high selectivity, such as to primary amines. The amination product generally is a mixture of primary, secondary and tertiary amines. Also it is difficult to separate the formed amines, such as the primary amine, from the starting alcohol since the boiling points may be very similar or close. For example, the boiling points of 2-ethylhexanol and 2-ethylhexyl amine are similar so that separation by distillation means is difficult.

There is need for a simple and efficient process for selectively producing higher alkylated amines from olefin feedstock, such as from higher alkylated, branched or dimer alcohols produced from olefin feedstock by the oxo process. The generally-known reactions comprise converting the alcohol to the corresponding aldehyde by dehydrogenation, followed by aldol reaction and amination with suitable amines to form amines having high molecular weight alkyl substituents such as detergent range hydrophobe groups. Reference is made to PCT application WO 85-02173, published Aug. 23, 1985, for its disclosure of processes for the production of high molecular weight amines from aldehydes derived from olefin feedstock by the oxo process.

Reference is also made to U.S. Pat. Nos. 4,152,353; 4,210,605 and 4,480,131 and to European Patent Application 034,480 published Aug. 26, 1981, for their disclosure of other known processes for producing amines from alcohols by dehydrogenation in the presence of an amine, followed by amination. The generally-accepted reaction mechanism involves dehydrogenating the alcohol to the aldehyde, aminating to form an imine and hydrogenating the imine to form the desired amine.

However the aforementioned reaction mechanism is difficult to accomplish in high yield with certain reactants and catalyst systems for several reasons. Firstly, we have found that water must be removed continuously from the reaction medium, but this is difficult to accomplish in the presence of an amine since most amines are hygroscopic and resist separation of water therefrom. Secondly, the essential catalyst may react and/or become less soluble in the reaction medium as the conversion of the alcohol to the imine proceeds, thereby stopping the reaction before all of the alcohol has been converted, and reducing the yield of amine.

Another potential problem relates to the instability of the intermediate imine, which is a Schiff base and therefore undergoes aldol-dimerization and is susceptible to conversion to polymeric products even under relatively mild reaction conditions in the presence of certain catalysts.

SUMMARY OF THE INVENTION

The present invention is based upon the discovery of a simple and efficient process, using a specific catalyst system for the dehydrogenation of aliphatic alcohols, particularly high molecular weight aliphatic alcohols including aliphatic ether alcohols derived from olefin feedstock in the presence of an aliphatic primary amine and under reflux reaction conditions, to selectively form corresponding aldehydes which are immediately reacted or trapped in situ with an aliphatic primary amine to form the corresponding imine, preferably in the presence of an azeotroping agent to assist with continuous water removal. Thereafter the imine can be subjected to reductive amination and/or hydrogenation in conventional manner to form the desired primary, secondary or tertiary amines.

The novel catalyst system for the critical dehydrogenation step of the present invention comprises a combination of zinc oxide, and/or a zinc salt of an organic acid, in a strong base such as an alkali metal hydroxide or alkaline earth metal hydroxide, including potassium hydroxide, sodium hydroxide, calcium hydroxide, barium hydroxide, beryllium hydroxide, etc. Dehydrogenation is carried out under gentle reflux conditions at a temperature between about 175° C. and 225° C., preferably about 190° C.-200° C., in the presence of a minor amount of the amine reactant, such as about 10% of the stoichiometric amount. Suitable zinc salts include salts of $C_2$ to $C_{20}$ aliphatic carboxylic acids including zinc acetate, zinc stearate, zinc 2-ethyl hexanoate, etc.

We have discovered that undesired side reactions are avoided and dehydrogenation proceeds smoothly provided that the dehydrogenation of the alcohol to the corresponding aldehyde is conducted in situ in the presence of a small amount of the primary amine reactant, added gradually as the reaction proceeds, and is accompanied by continuous removal of the reaction by-products, namely hydrogen gas released by the alcohol during dehydrogenation to form the transient aldehyde, and water formed during condensation of the aldehyde with the primary amine to form the imine (Schiff base), as illustrated by:

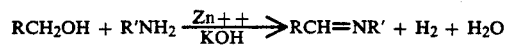

$$RCH_2OH + R'NH_2 \xrightarrow[KOH]{Zn++} RCH=NR' + H_2 + H_2O$$

The condensation of the transient aldehyde is so rapid that no complications of aldol formation result when the present process is applied to the conversion of oxo alcohols, including ether alcohols, to amines. Such $C_8$, $C_{10}$ and $C_{13}$ oxo alcohols are predominantly unbranched at the number two carbon atom and therefore aldehydes thereof can undergo aldol-like dimerization and possible further polymerization, which would frustrate the present reaction mechanism. However, as stated, the present condensation reaction takes place so rapidly that substantially no undesired polymerization occurs either with respect to the transient aldehyde or the unstable imine. Aldol-like dimerization of the imine is illustrated:

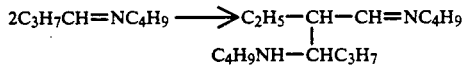

An essential step in the dehydrogenation of the alcohol or ether alcohol to the transient aldehyde, followed by condensation with the primary amine to form the imine, is the continuous removal of the water of condensation. Since most primary amines are hygroscopic, water cannot be distilled therefrom without substantial loss of the amine from the reaction medium. However we have found that the gradual addition of the proper primary amine, coupled with the addition of a hydrocarbon azeotroping agent, such as xylene or trimethylbenzene, enables the water of condensation to be selectively removed from the reaction medium as it is produced by the reaction between the aldehyde, formed in situ, and the primary amine which is gradually added so that preferably it is never present in the reaction medium in unreacted condition in an amount greater than about 10% of the stoichiometric amount, thus maintaining the solubility of the catalyst system in the reaction medium. The gradual addition of the amine is continued until the stoichiometrically-correct amount of amine has been added, most preferably until about 115% of the correct amount has been added.

Preferably the dehydrogenation step is conducted at a temperature between about 190° C. and 200° C., and the primary amine is gradually added as a 50/50 mixture with the azeotrope-forming liquid, i.e., trimethylbenzene, until vigorous reflux is achieved and all of the amine has been added. Batch reaction time is from two to eight hours, typically four hours.

As noted above, as the dehydrogenation reaction progresses the reaction medium or solvent for the catalyst changes from predominantly alcohol to predominantly imine. This adversely affects both the zinc ion and alkali metal hydroxide or alkaline earth metal hydroxide concentrations. The zinc will be more likely to precipitate as zinc oxide, since the contact with the hydroxide, such as potassium hydroxide, or alkoxide ion will be less. In turn, KOH will tend to precipitate since there is insufficient alcohol for solubilization.

After all of the amine/azeotrope material has been added and the reaction is completed, the reaction mixture is cooled, neutralized with acetic acid, separated and washed with water. Finally the washed organic liquid is heated under vacuum of 10-50 mm Hg to form the unsaturated dimer imine, in cases where the alkyl radical is susceptible to aldol-like dimerization reaction.

Further reaction of the imine to form the final amine is conducted in a manner which is conventional for producing amines from aldehydes as raw materials, i.e., using Raney nickel catalyst for reductive amination reactions, or using platinum catalyst for hydrogenation reactions to form secondary amines, both under mild conditions.

The following reactions are illustrative:

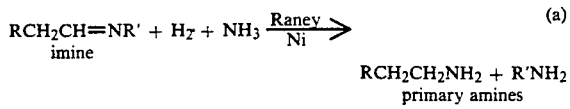

In cases where R' is —CH$_2$CH$_2$R, the end product is two moles of RCH$_2$CH$_2$NH$_2$, one of which can be recycled for further reaction with alcohol

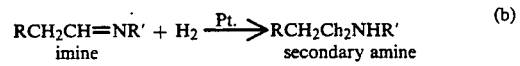

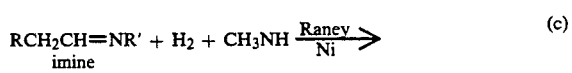

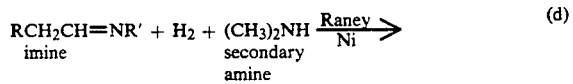

As noted, reactions (a) through (d) are relatively simple and proceed under mild conditions. It is the primary reaction of forming the imine from the starting alcohol which is extremely complex and which has been found to proceed efficiently and under mild reaction conditions as a result of the discovery of the use of the novel catalyst system of the present invention. The primary reaction may be illustrated:

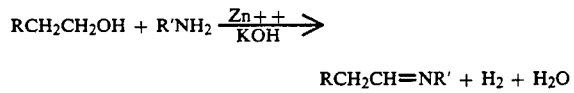

However the above reaction produces the intermediate aldehyde by dehydrogenation of the alcohol or ether alcohol, and the in situ aldehyde immediately reacts with the alkylamine, as quickly as it is generated, to form the imine, hydrogen gas and water. The alkylamine is added gradually for reaction with the aldehyde, as it is formed, so as not to disturb the solubility of the catalyst in the alcohol reaction medium, and the water is removed continuously to induce formation of the imine in relatively high yield.

We have found that the novel primary reaction of the present invention is suitable for the conversion of higher molecular weight Guerbet dimer alcohols to the corresponding amines. Also dimer alcohols, C$_{16}$ and C$_{20}$, as well as monomeric C$_8$, C$_{10}$ and C$_{13}$ oxo alcohols, and aliphatic ether alcohols found in oxo bottoms (up to C$_{26}$ but primarily C$_{20}$), all produced in various amounts in the oxo process of treating olefin feedstock, can be converted to the desired amines according to the present process.

The raw materials used in the primary reaction of the present invention are alcohols, including ether alcohols, and amines, both of which may be linear, branched or dimeric materials. Preferred alcohols are the higher molecular weight oxo alcohols, including ether alcohols, having from 20 to 26 carbon atoms, but alcohols having from about 6 to 50 carbon atoms generally are suitable.

Suitable amine feedstock can range from $C_1$ to $C_{50}$ primary aliphatic or alkyl amines, preferably from $C_1$ to $C_{24}$ primary alkyl amines.

In the foregoing formulas R represents an aliphatic group of 6 to 50 carbon atoms, preferably an unsubstituted alkyl group and R' represents an aliphatic group of 1 to 50 carbon atoms, preferably an unsubstituted alkyl group.

The amine and alcohol reactants are required in stoichiometrically-equivalent amounts but the amine preferably is added in an excess of about 15% in order to assure completeness of reaction.

The catalyst system for the critical primary reaction comprises a mixture of an alkali metal or alkaline earth metal hydroxide, preferably potassium hydroxide, and zinc oxide or a zinc salt of a linear or branched $C_2$-$C_{20}$ aliphatic carboxylic acid such as zinc acetate, zinc stearate, zinc 2-ethyl hexanoate, preferably zinc stearate. Zinc oxide also preferably is present in small amount with the zinc salt. The amount of alkali metal or alkaline earth metal hydroxide preferably is between about 0.1 mol and 0.6 mol per mol of starting alcohol, and the amount of zinc salt preferably is between about 0.01 mol and 0.02 mol per mol of starting alcohol.

A critical step of the present process involves the reaction of the starting alcohol to form the corresponding aldehyde. Such reaction is not favored by thermodynamics but is made possible by zinc catalysis coupled with the continuous conversion of the aldehyde to a Schiff base imine. The aldehyde is converted by reaction thereof with a primary amine, gradually added to the reaction mixture, and accompanied by removal of the water of reaction. Water cannot be removed from hygroscopic amines by simple refluxing and therefore it may be necessary to add an azeotroping agent, such as pseudocumene or mixed xylenes, which permit continuous reflux and water removal at the temperature of the imine-formation reaction. Preferably the amine and the azeotroping agent are added in controlled amounts so that the ratio of azeotroping agent to amine in the Dean Stark water trap is always greater than 1. This causes the water formed in the reaction to separate efficiently, whereby the reaction proceeds to favor imine-formation.

The reductive amination of the formed imine generally is conducted in conventional manner with a Raney nickel catalyst in the presence of an excess of amine or ammonia, preferably about three times the stoichiometric requirement. Combined hydrogen/ammonia pressures of about 400 psi are adequate although pressures up to about 800 psi have been found satisfactory. The reaction temperature is above 80°-90° C., preferably about 110° C., for completeness of reaction. Alcoholic solvent such as ethanol is preferred.

Therefore the most critical feature of the present process is the formation and trapping the imine from the transient aldehyde, under conditions which prevent hydrolysis and reversal of the reaction and which are compatible with the dehydrogenation catalyst system. Gradual addition of the primary amine is necessary to maintain solubility thereof in the reaction mixture. Otherwise continuous water removal is not possible and the imine-formation reaction is killed.

The following examples are set forth as illustrative of the production of high molecular weight imine mixture from high molecular weight alcohols obtained by subjecting olefin feedstock to the oxo process, followed by the conversion to the desired high molecular weight amines.

EXAMPLE 1

A 2-liter, 4-neck round-bottom flask was equipped with an air stirrer, thermometer, 50 ml Dean-Stark trap attached to a reflux condenser and a 500 ml dropping funnel. In the flask were placed 299.5 gm. of isooctyl alcohol (2.3 moles), 38.8 gm. of octylamine (0.3 mole), 50 gm. of KOH pellets and 30.0 gm. of zinc oxide powder. In the Dean-Stark trap was placed 52.0 gm. of a 75/25 solution of pseudocumene and octylamine. In the dropping funnel was placed 430.8 gm. of a 60/40 solution of octylamine/pseudocumene (2.0 moles amine).

The mixture was heated to reflux and the solution from the dropping funnel was added dropwise to maintain a pot temperature of 185° C. After 3.5 hours all had been added. The solution was refluxed for an additional 3.5 hours, during which time the pot temperature rose to 190° C., water evolution had ceased, and 36 ml of water had been collected.

The reaction mixture was cooled to room temperature. To this, 850 gm., was added 850 gm. of cyclohexane, 395 gm. butanol and 455 gm. pentanol. This mixture was filtered with a filter aid. The resulting clear and colorless liquid was washed twice with an equal weight of warm water. The layers were separated and the first aqueous layer was acidified with 90 gm. of 37% hydrochloric acid. An organic layer separated and was dissolved and extracted with two 80 gm. portions of pentanol. This organic solution was stripped of alcohol and the residue analyzed by gas chromatography (GC). The analysis indicated 86 gm. of isooctanoic acid, 21% of theory.

The organic layer containing the crude imine was placed in a distillation flask and stripped of solvent at reduced pressure, up to a pot temperature of 102° C. at 0.8 mm. The residue, 318.9 gm., was analyzed then heated at 110° C. and 10 mm Hg, for four hours. No distillate was collected. The residue was again analyzed after two hours and again after four hours. It was heated another hour at 120°/10 mm; and analyzed again. The results of these analyses are given in the following table.

| Hours Heated 10 mm Hg | % Octylamine | % $C_8/C_8$ Imine | % $C_{16}/C_8$ Imine | % Heavies |
| --- | --- | --- | --- | --- |
| 0 | 2.7 | 80.4 | 16.9 | — |
| 2 | 8.4 | 55.7 | 35.9 | — |
| 4 | 9.3 | 49.3 | 41.4 | 0.7 |
| 5 | 8.2 | 49.3 | 42.5 | 0.3 |

It was concluded from these data that the conversion to N-octyl-2-isohexylisodecylimine and octylamine is an equilibrium and thus will not proceed to completion in the presence of amine. The residue was heated again at 135° C. and 10 mm. for 3 hours and then analyzed, then heated an additional 2 hours at 100° C. and 0.2–0.3 mm. and analyzed again. Distillation of amine occurred in both cases. The analysis for the two samples were:

| Hours Heated 10 mm Hg | % Octylamine | % $C_8/C_8$ Imine | % $C_{16}/C_8$ Imine | % Heavies |
| --- | --- | --- | --- | --- |
| 3 | 4.1 | 37.6 | 57.1 | 1.5 |

-continued

| Hours Heated 10 mm Hg | % Octylamine | % C8/C8 Imine | % C16/C8 Imine | % Heavies |
|---|---|---|---|---|
| 5 | — | 24.4 | 72.1 | 3.2 |

Thus this final residue product, 232.9 gm, contained 167.9 gms of n-octyl-2-isohexylisodecylimine, or 42% of theoretical. The amount of N-octylisooctylimine was 56.8 gm., 10% of theory. The distillate obtained under high vacuum contained 30.3 gm. of N-octylisooctylimine, 6% of theory. Thus the summarized yields are isooctanoic acid 21%, N-octylisooctylimine 15%, N-octylisohexylisodecylimine 42% (79% total).

A sample of N-octyl-2-isohexylisodecylimine which had been distilled, b.p. 134°-151° C. at 0.03-0.04 mm., 25 gm. (0.07 mole), was dissolved in 25 gm. ethanol. To the cooled solution was added 19.7 gm. of methylamine (0.44 mole). This reaction mixture, with 3.6 gm. of Raney nickel was hydrogenated in the Parr vessel at 800 psi hydrogen. After filtration, the product was filtered to remove the Raney nickel and analyzed by GC. This showed 35.3% octylamine, 59.7% N-methyl-2-isohexylisodecylamine and 3.5% heavies. Distillation gave pure N-methyl-2-isohexylisodecylamine, heart cut b.p. 95° C. at 0.10 mm. Analysis: Calculated for $C_{17}H_{37}N$; % C, 79.92; % H, 14.40; % N, 5.48. Found. % C, 79.60; % H, 14.31; % N, 5.20. IR and NMR spectra were consistent with the proposed structure.

The above procedure was repeated except that dimethylamine was used instead of methylamine. Similar results were obtained, except that the hydrogenation step was slower. It was concluded that the ease of hydrogenation decreases in the series $H_2/NH_3 > H_2/CH_3NH_2 > H_2/(CH_3)_2NH$.

EXAMPLE 2

A four neck, round bottom flask was fitted with a magnetic stirring bar, thermowell with thermocouple and temperature controller, a 50 ml. Dean-Stark trap fitted with a reflux condenser, and a flask for adding liquid dropwise.

In the flask were placed 364 gms Oxo isodecyl alcohol, 25.9 gms n-octylamine, 60 gms potassium hydroxide, 23.5 gms zinc stearate, and 2.9 gms zinc oxide. While stirring, the mixture was heated to 198° C. At this temperature, a solution of 318 gms n-octylamine and 318 gms trimethyl benzene was added dropwise at such a rate as to maintain vigorous reflux. Water was collected as a lower layer in the Dean-Stark trap. After 2 hours of reflux, 368 gms of the octylamine/trimethylbenzene mixture had been added, and 29 g. of water had collected in the Dean-Stark trap. During the next two hours, the remainder of the octylamine/trimethylbenzene mixture was added while allowing the reaction mixture reflux temperature to lower to 185° C. At the end of this period, the product, a hazy solution, was cooled and a sample taken for analysis. An aqueous solution of acetic acid was added to neutralize the potassium hydroxide, separated, and the organic layer washed with water. Analysis by gas chromatography indicated 46.3% conversion to n-octylisodecyl imine and 51.1% conversion to n-octylisoeicosyl imine.

The imine mixture can be reduced to produce a mixture of secondary amines by reaction with hydrogen in the presence of a platinum catalyst, according to the following reactions:

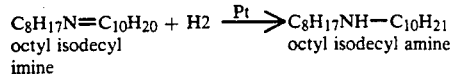
octyl isodecyl imine

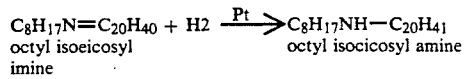
octyl isoeicosyl imine

The imine mixture can be reductively aminated with hydrogen and ammonia in the presence of a Raney nickel catalyst to form primary amines according to the following reactions:

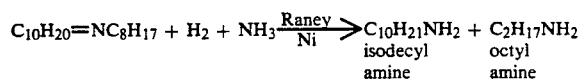
                        isodecyl    octyl
                        amine      amine The imine mixture can be reductively aminated to produce a mixture of primary and secondary amines by reaction with hydrogen and a primary amine such as methyl amine in the presence of Raney nickel catalyst, according to the following reactions:

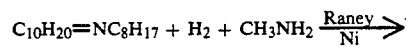

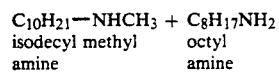
isodecyl methyl    octyl
amine              amine

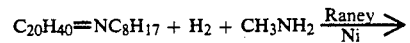

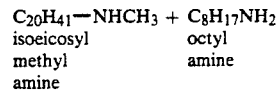
isoeicosyl    octyl
methyl       amine
amine

The imine mixture can be reductively aminated to produce a tertiary amine and a primary amine by reaction with hydrogen and a secondary amine such as dimethyl amine in the presence of Raney nickel catalyst according to the following reactions:

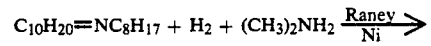

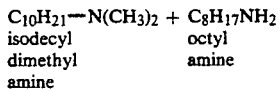
isodecyl    octyl
dimethyl  amine
amine

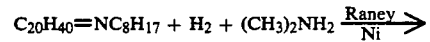

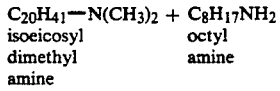
isoeicosyl   octyl
dimethyl  amine
amine

EXAMPLE 3

A mixture of N-octylisodecylimine and N-octyl-2-isooctylisododecylimine was prepared according to the procedure of Examine 1. The washed and stripped residue product analyzed 40.7% $C_{10}/C_8$ imine and 57.2% $C_{20}/C_8$ imine. A 20.0 gm. sample was dissolved in 40 gm. of ethanol. The yellow solution was chilled and 7.2 gm. of ammonia was added by gaseous transfer. This solution, along with 7.2 gm. of Raney nickel, was placed in the Parr autoclave and the hydrogenation was conducted at 400-300 psi and 100° C.

The hydrogenated product, after filtration, analyzed 34.1% octylamine, 20.6% isodecylamine, 44.0% isooctylisododecylamine, 0.3% untreated $C_{20}/C_8$ imine and/or N-octyl-2-isooctylisododecylamine and 1.0% unknown heavies (excluding ethanol from the analysis). The theoretical composition of the product is 36.5% octylamine, 23.0% isodecylamine and 40.5% 2-isooctylisododecylamine.

In this example, the solution in ethanol was relatively dilute and a high quantity of Raney nickel was employed. These conditions had been found to minimize the undesired components, i.e., untreated or hydrogenated $C_{20}/C_8$ imine (H-1) and unknown heavies (H-2). The effects of less ethanol and less Raney nickel are tabulated below:

| Run No. | % Ethanol | gms. Ni | % H-1 | % H-2 |
|---|---|---|---|---|
| 1 | 67 | 7.2 | 0.4 | 0.8 |
| 2 | 67 | 3.6 | 2.7 | 1.3 |
| 3 | 67 | 1.8 | 9.6 | 6.2 |
| 4 | 50 | 3.6 | 7.2 | 6.0 |

Seven batches of material prepared as in Run No. 1 were combined. The alcohol was stripped off at reduced pressure, after which the residual amines were distilled, 2-isooctylisododecylamine distilled at 133°-145° C. at 0.3-0.4 mm. This distillate gave only a single retention in the GC. The $1_H$ NMR spectrum was consistent with primary amine, but showed some residual unsaturation. Analysis: Calculated for $C_{20}H_{43}N$: % C, 80.73; % H, 14.57; % N, 4.71. Found: % C, 81.50; H, 13.66; N, 5.11. Calculated for $C_{20}H_{41}N$: % C, 81.28; % H, 13.98; % N, 4.74.

The formation of heavy components was at the expense of the formation of $C_{20}$ amine. Thus in Run No. 3 above, only 23.8% of $C_{20}$ amine was formed, compared to the 40.5% expected. It appears that a portion of the N-octyl-2-isooctylisododecylimine, possibly the more branched and stericially hindered, is more difficult to reductively aminate.

EXAMPLE 4

N-Dodecyl-2-ethylhexylimine prepared as described in Example 1, 35.0 g. (0.12 mol), was dissolved in 35 gm. of ethanol. This solution was chilled in an ice bath and 5.9 gm. of ammonia (0.35 mole) was added by gaseous transfer. This solution, together with 3.6 gm. of wet Raney nickel which had been washed with ethanol, was added to a 150 ml Parr autoclave equipped with a magnetic stirrer. The autoclave was sealed, flushed with nitrogen, then pressurized with 314 psi hydrogen. The autoclave and contents were heated with stirring to 140° C., and the pressure dropped to 234 psi during the heating. Hydrogen was added to 300 psi and heating continued for a total of 2 hours. Only a slight further drop occurred.

The vessel was cooled, vented, and purged with nitrogen. The contents were removed and filtered to remove the catalyst. The colorless product solution was analyzed by GC. Exclusive of ethanol solvent, the analysis showed 36.2% 2-ethylhexylamine, 55.3% dodecylamine, 0.8% unreacted imine and 3.7% hydrogenated imine (N-dodecyl-N-2-ethylhexylamine). The found ratio of $C_{12}$ amine/$C_8$ amine is 1.53/1.0, theoretical ratio is 1.43/1.0.

EXAMPLE 5

A four-neck, two liter round bottom flask was fitted with an air driven paddle stirrer, thermometer, 500 ml dropping funnel and two 30 ml Dean-Stark traps with attached reflux condensers. Into the flask were placed 484.9 g (2.0 mole) of hexadecyl alcohol, 372.7 g (2.4 mole) n-1-decylamine, 60 g potassium hydroxide, 20.0 g of zinc stearate and 8.0 g of zinc oxide. Into each of the Dean-Stark traps was placed 30.4 g of pseudocumene. Into the dropping funnel was placed 365.4 g of pseudocumene. The flask and contents were heated with air stirring to 198° C. and a total of 259.5 g pseudocumene was added dropwise over a period of three hours to maintain reflux at this temperature. The reaction mixture was heated an additional two hours at 198° C. During the total five hour heating period, 36 g water was evolved. During this period, considerable white solid precipitated.

After cooling to room temperature, a solution of 60.0 g acetic acid in 140 g water was added and the mixture was stirred for 20 minutes, then filtered. The layers were separated and the aqueous lower layer was discarded. An analysis of the upper layer indicated that 11% of hexadecyl alcohol remained unconverted. With the exception of the unanalyzed acid, the remainder was converted to N-decyl-2-isohexylisodecyl imine.

This experiment and other similar ones indicate that very high conversions are difficult if the catalyst becomes insoluble as the reaction proceeds and solvent alcohol is consumed. This is important since residual alcohol cannot be separated from the corresponding amine if this is the desired final product (after reductive amination of the intermediate imine). N-Decylamine is a good agent for imine preparation since it has a higher boiling point than octylamine, which is the usual reagent, and is not solid as is n-dodecylamine. Unfortunately, n-decylamine is not readily available. However, it is anticipated that a branched $C_{10}$ amine would be ideal as the imination agent. Finally, the constant reaction temperature for reflux, while condensation is occurring, is due to a fortuitous counterbalance of volatilities since one slightly volatile compound (decylamine) is consumed while the mole fraction of the most volatile component (pseudocumene) increases.

A reaction conducted in the same manner as outlined above, but with n-octylamine, gave only 51% conversion to N-octyl-2-isohexylisodecylamine after 5.5 hours reaction at 195° C. This further illustrates the decreased efficiency of octylamine for water removal.

In a similar reaction, mixed xylenes were used as the azeotroping agent and octylamine was used as the amine for making the imine. The flask and apparatus was the same as before. In the flask were placed 484.4 gm. (2.0 moles) of $C_{16}$ dimer alcohol, 51.6 gms. (0.4 mole) of octylamine, 40.0 gm. KOH and 20.0 gm. of zinc stearate. The Dean-Stark trap was filled with mixed xylenes. The mixture was heated to 195° C. and sufficient mixed xylenes (50.4 gm.) was added to cause reflux to begin. Then octylamine was added dropwise from the dropping funnel to maintain reflux at a pot temperature of 195° C. During three hours reaction, 275 ml of octylamine was added and 28 ml water was evolved. The flask was cooled and sampled, then reheated to 195° C. Xylenes (46 ml) were added to cause reflux. Heating was continued for another three hours, during which time 105 ml of octyl amine was added and 3 ml of water was evolved.

After neutralizing with acetic acid as before, the 3-hour and final samples were analyzed by GC. The conversions of alcohol to amine were 60% and 79%, respectively.

This indicates that xylenes, being more volatile, are more effective, as an azeotroping agent. The central and critical feature, in any case, is to maintain a vapor composition rich in hydrocarbon, >50%, in order to cause water to separate efficiently in the Dean-Stark.

In a typical distillation, the crude product was washed with water after neutralization of the KOH with acetic acid. The washed material was distilled directly with high vacuum and without any fractionation column (the distillation head was connected directly to the pot). From a preparation utilizing 2.0 moles of isohexylisodecyl alcohol, with 80% conversion of the alcohol, 1016 gm of crude product was distilled. A pure fraction of N-octyl-2-isohexylisodecylimine, 355 gm. >99% imine, distilled at 140°–144° C. at 0.02–0.03 mm Hg. Another 65 gm. of imine of 91% purity was obtained. The yield of distilled imine was 60%, based on alcohol charged, or 75% based on alcohol converted.

Reductive amination is conducted as in the preceding Examples.

It is to be understood that the above described embodiments of the invention are illustrative only and that modifications throughout may occur to those skilled in the art. Accordingly, this invention is not to be regarded as limited to the embodiments disclosed herein but is to be limited as defined by the appended claims.

We claim:

1. Process for the selective production of high molecular weight aliphatic imines from corresponding high molecular weight aliphatic alcohols, including ether alcohols, comprising the steps of:
   (a) forming a mixture of a high molecular weight $C_6$–$C_{26}$ aliphatic alcohol, and a dehydrogenation catalyst system consisting essentially of zinc oxide and/or zinc salt of $C_2$–$C_{20}$ aliphatic carboxylic acid, and a strong base comprising an alkaline earth hydroxide or alkali metal hydroxide of a metal selected from the group consisting of potassium, sodium, calcium, barium and beryllium;
   (b) heating said mixture to a refluxing temperature between about 175° C. and 225° C. while gradually adding thereto a sufficient amount of a $C_1$–$C_{24}$ primary aliphatic amine to produce an amount thereof at least equimolar to the aliphatic alcohol in said mixture, and while continuously removing water, to dehydrogenate said aliphatic alcohol to form the corresponding aldehyde and to immediately react said aldehyde with said primary amine to form the corresponding aliphatic imine, and
   (c) neutralizing the reaction mixture of step (b) and isolating said aliphatic imine.

2. Process according to claim 1 in which said aliphatic alcohol is an oxo alcohol.

3. Process according to claim 1 in which said aliphatic alcohol is a dimer alcohol.

4. Process according to claim 1 in which said catalyst system comprises an alkali metal hydroxide.

5. Process according to claim 1 in which said zinc salt comprises zinc stearate.

6. Process according to claim 5 in which said catalyst system further comprises a minor amount of zinc oxide.

7. Process according to claim 1 in which the mixture of step (a) also includes a minor amount of said primary aliphatic amine.

8. Process according to claim 1 in which a hydrocarbon azeotroping agent is also present in the mixture of step (a).

9. Process according to claim 1 in which a hydrocarbon azeotroping agent selected from the group consisting of xylene and trimethyl benzene is also added gradually to said mixture in step (b).

10. Process for producing a high molecular weight aliphatic amine according to claim 1 in which the imine isolated in step (c) is reductively aminated to form a high molecular weight aliphatic amine.

11. Process according to claim 10 in which said imine is reductively aminated in the presence of ammonia to form a high molecular weight primary aliphatic imine.

12. Process according to claim 10 in which said imine is reductively aminated in the presence of an aliphatic primary amine to form a high molecular weight secondary aliphatic amine.

13. Process according to claim 10 in which said imine is reductively aminated in the presence of an aliphatic secondary amine to form a high molecular weight tertiary aliphatic amine.

14. Process according to claim 10 in which said reductive amination is conducted in the presence of a Raney nickel catalyst.

15. Process for the selective production of high molecular weight aliphatic imines from corresponding high molecular weight aliphatic alcohols, including ether alcohols, comprising the steps of:
   (a) forming a mixture of a high molecular weight $C_6$–$C_{26}$ aliphatic alcohol, and a dehydrogenation catalyst system consisting essentially of between about 0.1 and 0.6 mol, per mol of alcohol, of zinc oxide and/or a zinc salt of an $C_2$–$C_{20}$ aliphatic carboxylic acid, and between about 0.01 and 0.02 mol, per mol of the alcohol, of a strong base comprising a hydroxide of a metal selected from the group consisting of potassium, sodium, calcium, barium and beryllium;
   (b) heating said mixture to a refluxing temperature between about 175° C. and 225° C. while gradually adding thereto a mixture comprising a hydrocarbon azeotroping agent and a sufficient amount of a $C_1$–$C_{24}$ aliphatic amine to produce an amount thereof at least equimolar to the aliphatic alcohol in said mixture, and while continuously removing an azeotropic mixture of said hydrocarbon azeotroping agent and water to dehydrogenate said aliphatic alcohol to form the corresponding aldehyde and to immediately react said aldehyde with said primary amine to form the corresponding aliphatic imine, and
   (c) neutralizing the reaction mixture of step (b) and isolating said aliphatic imine.

16. Process according to claim 15 in which said aliphatic alcohol is an oxo alcohol.

17. Process according to claim 15 in which said aliphatic alcohol is a dimer alcohol.

18. Process according to claim 15 in which said catalyst system comprises an alkali metal hydroxide.

19. Process according to claim 15 in which said zinc salt comprises zinc stearate.

20. Process according to claim 15 in which said catalyst system further comprises a minor amount of zinc oxide.

21. Process according to claim 15 in which said primary aliphatic amine is a $C_1$-$C_{24}$ linear aliphatic amine.

22. Process according to claim 15 in which the mixture of step (a) also includes a minor amount of said primary aliphatic amine.

23. Process according to claim 15 in which a hydrocarbon azetroping agent selected from the group consisting of xylene and trimethyl benzene is also present in the mixture of step (a).

24. Process according to claim 15 in which a hydrocarbon azetroping agent selected from the group consisting of xylene and trimethyl benzene is also added gradually to said mixture in step (b).

25. Process for producing a high molecular weight aliphatic amine according to claim 15 in which the amine isolated in step (c) is reductively aminated to form a high molecular weight aliphatic amine.

26. Process according to claim 25 in which said imine is reductively aminated in the presence of ammonia to form a high molecular weight primary aliphatic imine.

27. Process according to claim 25 in which said imine is reductively aminated in the presence of an aliphatic primary amine to form a high molecular weight secondary aliphatic amine.

28. Process according to claim 25 in which said imine is reductively aminated in the presence of an aliphatic secondary amine to form a high molecular weight tertiary aliphatic amine.

29. Process according to claim 25 in which said reductive amination is conducted in the presence of a Raney nickel catalyst.

* * * * *